(12) United States Patent
Jiang et al.

(10) Patent No.: US 11,298,147 B2
(45) Date of Patent: Apr. 12, 2022

(54) MINIMALLY INVASIVE SURGICAL DEVICE

(71) Applicant: Industrial Technology Research Institute, Hsinchu (TW)

(72) Inventors: Ching-Chuan Jiang, New Taipei (TW); Hsin-Hsin Shen, Hsinchu County (TW); Ming-Chia Yang, Taipei (TW); Yun-Han Lin, Taichung (TW); Wei-Hong Chang, Yunlin County (TW)

(73) Assignee: Industrial Technology Research Institute, Hsinchu (TW)

( * ) Notice: Subject to any disclaimer, the term of this patent is extended or adjusted under 35 U.S.C. 154(b) by 179 days.

(21) Appl. No.: 15/909,986

(22) Filed: Mar. 1, 2018

(65) Prior Publication Data

US 2018/0250030 A1  Sep. 6, 2018

Related U.S. Application Data

(60) Provisional application No. 62/466,380, filed on Mar. 3, 2017.

(51) Int. Cl.
*A61B 17/32* (2006.01)
*A61B 17/16* (2006.01)
(Continued)

(52) U.S. Cl.
CPC .... *A61B 17/32002* (2013.01); *A61B 17/1617* (2013.01); *A61B 17/1662* (2013.01);
(Continued)

(58) Field of Classification Search
CPC .............. A61B 17/32; A61B 17/32002; A61B 2017/320004; A61B 2017/320032;
(Continued)

(56) References Cited

U.S. PATENT DOCUMENTS 5,236,289 A * 8/1993 Salyer ..................... B23B 31/08
                                               279/16
5,437,630 A    8/1995 Daniel et al.
(Continued)

FOREIGN PATENT DOCUMENTS

CN    87201666     5/1988
CN    202942174    5/2013
(Continued)

OTHER PUBLICATIONS

"Office Action of China Counterpart Application," dated Nov. 5, 2019, p. 1-p. 9.

(Continued)

*Primary Examiner* — Darwin P Erezo
*Assistant Examiner* — Christian D. Knauss
(74) *Attorney, Agent, or Firm* — JCIPRNET

(57) ABSTRACT

A minimally invasive surgical device includes a main body, a buffer assembly and a cutter bit. The main body includes an inner tube and an outer tube, wherein the inner tube is disposed in the outer tube. An end of the buffer assembly is connected to the inner tube. The cutter bit is connected to another end of the buffer assembly, wherein the cutter bit has a cutting portion. When the cutting portion is in contact with an object, the buffer assembly is adapted to enable the cutter bit to move relatively to the inner tube to decrease a cutting force between the cutting portion and the object, and is adapted to enable the cutting portion to be tilted with a surface of the object.

14 Claims, 9 Drawing Sheets

(51) Int. Cl.
  *A61B 90/00* (2016.01)
  *A61B 17/00* (2006.01)
(52) U.S. Cl.
  CPC ......... *A61B 17/162* (2013.01); *A61B 17/1628* (2013.01); *A61B 17/1631* (2013.01); *A61B 17/1659* (2013.01); *A61B 2017/00862* (2013.01); *A61B 2017/1602* (2013.01); *A61B 2017/320032* (2013.01); *A61B 2090/031* (2016.02)
(58) Field of Classification Search
  CPC  A61B 2017/32004; A61B 2017/32007; A61B 2017/320071; A61B 17/1624; A61B 17/1664; A61B 17/1666; A61B 17/1668; A61B 17/1684; A61B 17/1615; A61B 17/1617; A61B 17/162; A61B 17/1631; A61B 17/1633; A61B 17/1659; A61B 2090/031; A61B 17/00234; F16D 3/265; F16D 3/28; F16D 3/34; F16D 3/36
  See application file for complete search history.

(56) References Cited

U.S. PATENT DOCUMENTS

| | | | |
|---|---|---|---|
| 5,810,809 A | 9/1998 | Rydell | |
| 5,913,867 A | 6/1999 | Dion | |
| 6,645,218 B1* | 11/2003 | Cassidy | A61B 17/32002 606/170 |
| 7,077,845 B2 | 7/2006 | Hacker et al. | |
| 8,617,164 B2 | 12/2013 | Nelson et al. | |
| 8,663,264 B2 | 3/2014 | Cesarini et al. | |
| 8,870,747 B2 | 10/2014 | Moreno, Jr. et al. | |
| 8,968,306 B2 | 3/2015 | Unger | |
| 9,559,624 B2 | 1/2017 | Philipp | |
| 2002/0038129 A1* | 3/2002 | Peters | A61B 17/32002 606/167 |
| 2005/0203527 A1* | 9/2005 | Garrison | A61B 17/1617 606/80 |
| 2006/0196038 A1 | 9/2006 | Van Wyk | |
| 2010/0057087 A1* | 3/2010 | Cha | A61B 17/1633 606/80 |
| 2011/0118789 A1 | 5/2011 | Siegal | |
| 2012/0031219 A1* | 2/2012 | Isobe | A61B 17/1633 74/490.04 |
| 2014/0018816 A1* | 1/2014 | Fenn | A61B 17/8875 606/104 |
| 2015/0354635 A1 | 12/2015 | Mcclymont et al. | |
| 2016/0135834 A1 | 5/2016 | Bleich et al. | |
| 2016/0331385 A1 | 11/2016 | Stoll et al. | |

FOREIGN PATENT DOCUMENTS

| | | |
|---|---|---|
| CN | 203328761 | 12/2013 |
| CN | 204274560 | 4/2015 |
| CN | 205144657 | 4/2016 |
| CN | 205339073 | 6/2016 |
| CN | 205729453 | 11/2016 |
| CN | 106344107 | 1/2017 |
| CN | 106344108 | 1/2017 |
| CN | 104434257 | 8/2017 |
| EP | 0957786 | 11/2003 |
| EP | 1410763 | 4/2004 |
| EP | 2412320 | 11/2013 |
| EP | 3028654 | 1/2017 |
| JP | 6072379 | 2/2017 |
| TW | I584775 | 6/2017 |
| WO | 2008048449 | 4/2008 |
| WO | 2012037137 | 3/2012 |

OTHER PUBLICATIONS

"Notice of Allowance of Taiwan Counterpart Application," dated Sep. 25, 2018, pp. 1-3.
"Search Report of Europe Counterpart Application", dated Jul. 3, 2018, p. 1-p. 194.
"Search Report of Europe Counterpart Application", dated Apr. 12, 2019, p. 1-p. 5.
"Office Action of China Counterpart Application", dated Jul. 17, 2020, p. 1-p. 6.

* cited by examiner

MINIMALLY INVASIVE SURGICAL DEVICE

CROSS-REFERENCE TO RELATED APPLICATION

This application claims the priority benefit of U.S. provisional application Ser. No. 62/466,380, filed on Mar. 3, 2017. The entirety of the above-mentioned patent application is hereby incorporated by reference herein and made a part of this specification.

TECHNICAL FIELD

The invention relates to a surgical device. More particularly, the invention relates to a minimally invasive surgical device.

RELATED ART

Recently, together with the improvement of the living standard, the extension of lifespan, changes to diets of people (more foods containing nuclear protein), and the rise in the obesity rates, diseases arising from our skeletal system weakened as we age are more and more prevalent, such as degenerative spine conditions, osteoarthritis, and so on. In general, these diseases may be treated by endoscopic resection; however, the existing endoscopic resection cannot effectively remove joint protrusions or crystallized materials, and thus damages still lie in cartilage. The limited capacity for self-repair and regeneration of cartilage tissues leads to the vulnerability of cartilage and failure to self recovery, and patients can only replace the joints after the abrasion issue of articular cartilage remains unresolved to certain extent.

SUMMARY OF INVENTION

The invention relates to a minimally invasive surgical device that can effectively remove joint protrusions or crystals.

In the invention, a minimally invasive surgical device including a main body, a buffer assembly, and a cutter bit is provided. The main body includes an inner tube and an outer tube, and the inner tube is disposed in the outer tube. One end of the buffer assembly is connected to the inner tube. The cutter bit is connected to the other end of the buffer assembly, and the cutter bit has a cutting portion. When the cutting portion is in contact with an object, the buffer assembly is adapted to enable the cutter bit to move relatively to the inner tube to decrease a cutting force between the cutting portion and the object, and is adapted to enable the cutting portion to be tilted along with a surface of the object.

According to an embodiment of the invention, the buffer assembly includes an elastic member connected between the inner tube and the cutter bit.

According to an embodiment of the invention, the elastic member is a compression spring, a leaf spring, or elastic polymer.

According to an embodiment of the invention, the buffer assembly includes a universal joint connected between the elastic member and the cutter bit.

According to an embodiment of the invention, the universal joint includes a first connection member and a second connection member, the first connection member has a convex spherical surface, the second connection member has a concave spherical surface and is movably connected to the convex spherical surface through the concave spherical surface, the cutter bit is connected to the first connection member, and the elastic member is connected to the second connection member.

According to an embodiment of the invention, the universal joint includes a first connection member and a second connection member, the first connection member has an accommodation cavity, the second connection member has a plurality of inclined surfaces and is movably disposed in the accommodation cavity, an inner surface of the accommodation cavity is adapted to lean against any of the inclined surfaces to enable the first connection member to be tilted, the cutter bit is connected to the first connection member, and the elastic member is connected to the second connection member.

According to an embodiment of the invention, the inner tube has at least one concave portion, and the first connection member has at least one convex portion and is movably connected to the at least one concave portion through the at least one convex portion.

According to an embodiment of the invention, the second connection member has an arc surface relative to the inclined surfaces and movably leans against the elastic member through the arc surface.

According to an embodiment of the invention, the minimally invasive surgical device further includes a driver unit adapted to drive the cutter bit to rotate.

According to an embodiment of the invention, the driver unit is connected between the buffer assembly and the cutter bit and adapted to drive the cutter bit to rotate relatively to the inner tube.

According to an embodiment of the invention, the driver unit includes an actuator and a gear set, the actuator is connected to the buffer assembly, and the gear set is connected between the actuator and the cutter bit.

According to an embodiment of the invention, the driver unit is connected to the inner tube and adapted to drive the inner tube and the cutter bit to rotate together relatively to the outer tube.

According to an embodiment of the invention, the cutter bit has at least one hole, and sawdust generated after the object is cut by the cutting portion is discharged along the main body after passing through the at least one hole.

According to an embodiment of the invention, the minimally invasive surgical device further includes a suction supply portion, wherein the sawdust generated after the object is cut by the cutting portion is adapted to move along the main body by a suction force provided by the suction supply portion.

According to an embodiment of the invention, an outer diameter of the cutter bit is less than 10 millimeters.

According to an embodiment of the invention, the buffer assembly is at least partially disposed in the inner tube, the inner tube has a stopper, and the buffer assembly leans against the stopper.

In view of the above, the minimally invasive surgical device provided in one or more exemplary embodiments can reduce the cutting force between the cutting portion of the cutter bit and the operated object (such as the joint with bone protrusions and crystallized materials) by the buffer assembly, so as to avoid unexpected damages to the operated object itself due to the excessive cutting force. Besides, the buffer assembly of the minimally invasive surgical device provided in one or more exemplary embodiments enables the cutting portion of the cutter bit to be tilted along the surface of the operated object; thereby, the cutting portion is able to effectively remove the joint protrusions or the crystallized materials along the extension direction of the surface of the operated object.

To make the above features and advantages provided in one or more of the embodiments of the invention more comprehensible, several embodiments accompanied with drawings are described in detail as follows.

DETAILED DESCRIPTION OF EMBODIMENTS

Figure 1:
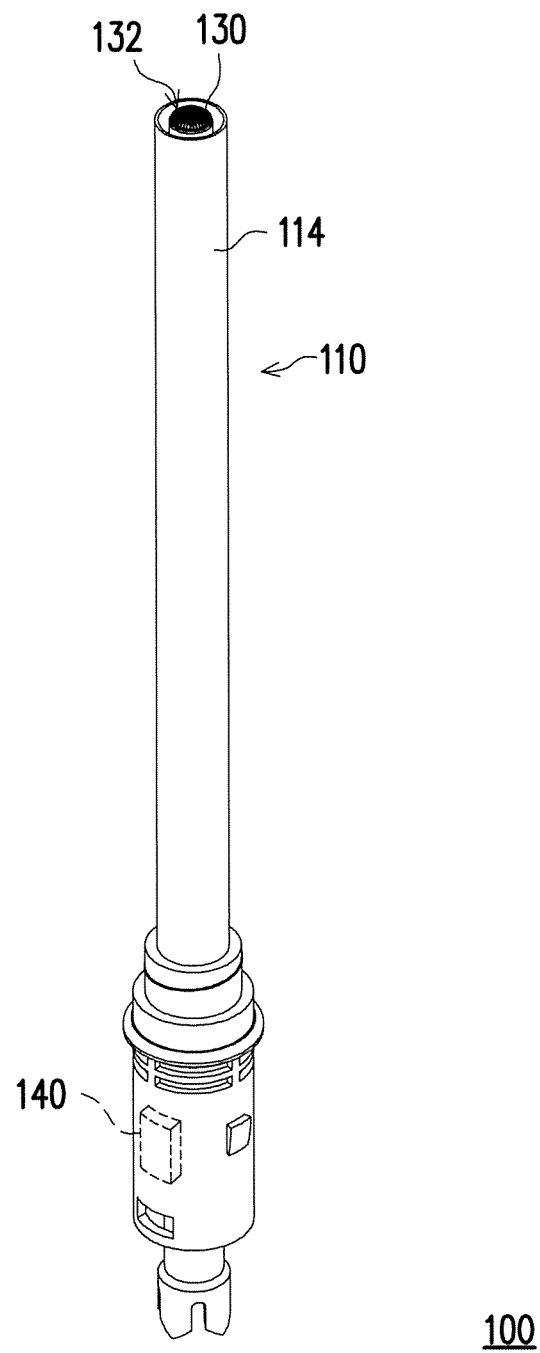
FIG. 1 is a three-dimensional view of a minimally invasive surgical device according to an embodiment of the invention.
Figure 2:
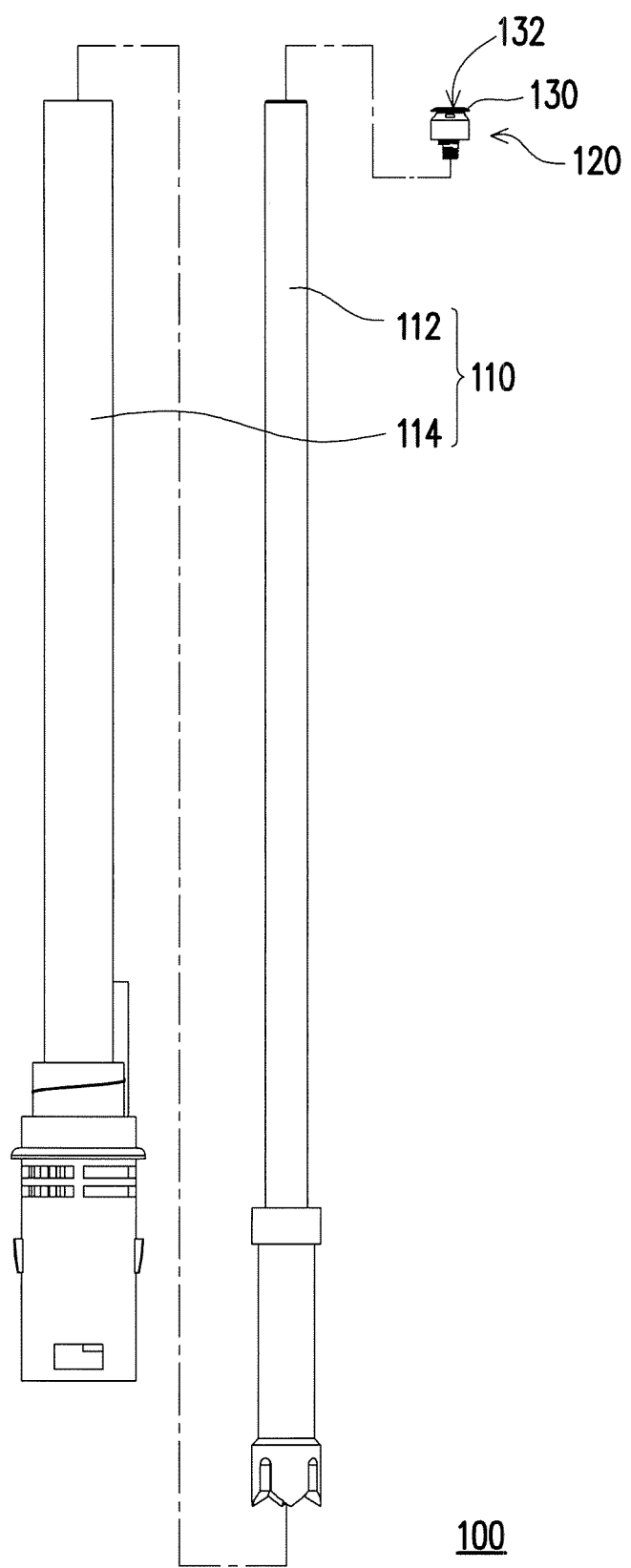
FIG. 2 is an exploded view of the minimally invasive surgical device depicted in FIG. 1.

FIG. 1 is a three-dimensional view of a minimally invasive surgical device according to an embodiment of the invention. FIG. 2 is an exploded view of the minimally invasive surgical device depicted in FIG. 1. With reference to FIG. 1 and FIG. 2, the minimally invasive surgical device 100 provided in the present embodiment is a surgical device configured to remove bone protrusions or crystallized materials in human joints and includes a main body 110, a buffer assembly 120, and a cutter bit 130. The main body 110 includes an inner tube 112 and an outer tube 114. The inner tube 112 is disposed within the outer tube 114. One end of the buffer assembly 120 is connected to the inner tube 112, and the cutter bit 130 is connected to the other end of the buffer assembly 120. The cutter bit 130 has a cutting portion 132, i.e., a blade of the cutter bit 130.

In the present embodiment, the outer diameter of the cutter bit 130 is less than 10 millimeters, for instance, so as to better perform the minimally invasive surgery; however, this should not be construed as a limitation to the invention. Besides, the inner tube 112 provided in the present embodiment may be connected to a proper driver unit (e.g., a motor) through a connection portion at the rear end of the inner tube 112, so as to drive the inner tube 112 and the cutter bit 130 by the driver unit to rotate together relatively to the outer tube 114 and thereby perform the cutting action. In other embodiments, the driver unit may be a component included in the minimally invasive surgical device 100 and is connected to the inner tube 112.

During the minimally invasive surgery, when the cutting portion 132 of the cutter bit 130 is in contact with an operated object (where the surgical operation is performed, such as the joint with bone protrusions and crystallized materials), the butter assembly 120 is adapted to enable the cutter bit 130 to move relatively to the inner tube 112 to reduce the cutting force between the cutting portion 132 and the operated object and thus protect the operated object from unexpected damages due to the excessive cutting force. Besides, the buffer assembly 120 is adapted to enable the cutting portion 132 to be tilted together with the surface of the operated object; thereby, the cutting portion 132 is able to effectively remove the joint protrusions or the crystallized materials along the extension direction of the surface of the operated object.

Figure 3:
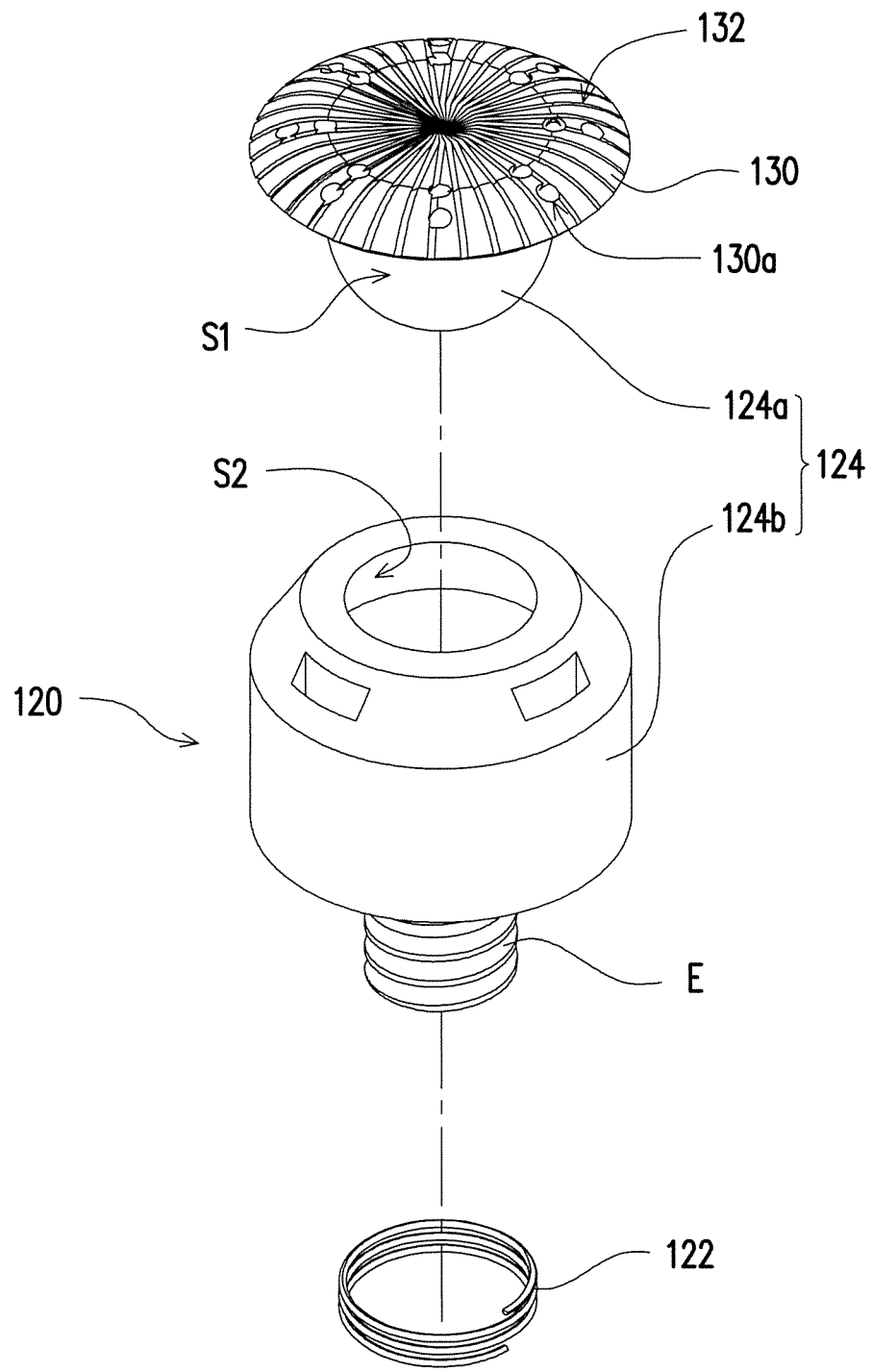
FIG. 3 is an exploded view of the cutter bit and the buffer assembly depicted in FIG. 2.
Figure 4:
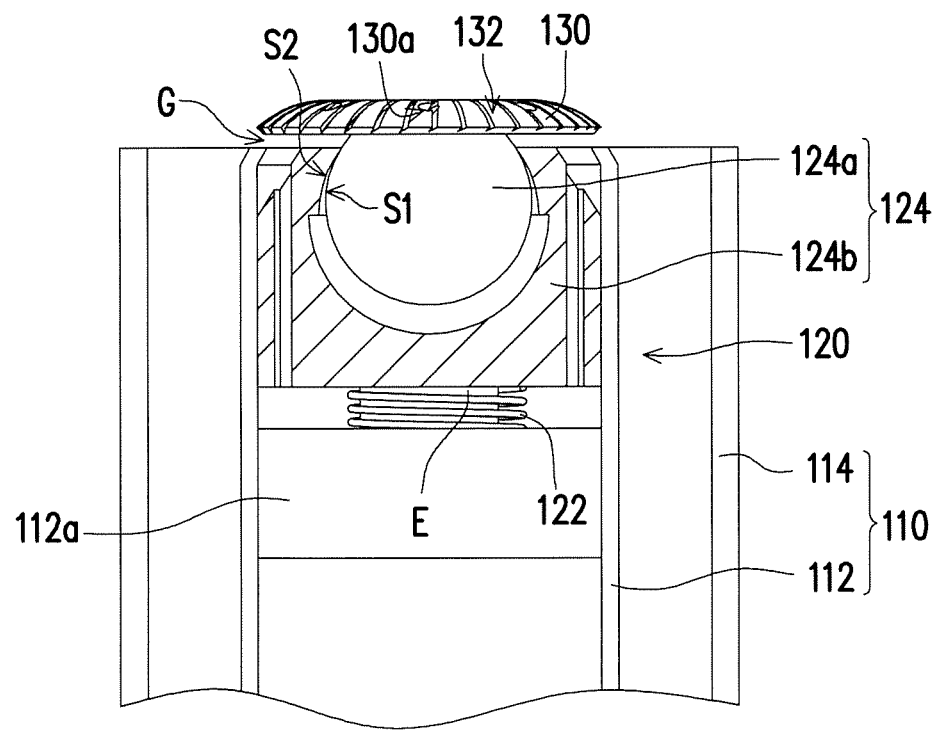
FIG. 4 illustrates a partial structure of the minimally invasive surgical device depicted in FIG. 1.

FIG. 3 is an exploded view of the cutter bit and the buffer assembly depicted in FIG. 2. FIG. 4 illustrates a partial structure of the minimally invasive surgical device depicted in FIG. 1. With reference to FIG. 3 and FIG. 4, specifically, the buffer assembly 120 provided in the present embodiment is at least disposed in the inner tube 112 and includes an elastic member 122 connected between the inner tube 112 and the cutter bit 130. The elastic member 122 is, for instance, a compression spring and by virtue of its elastic deformability enables the cutter bit 130 to move relatively to the inner tube 112 as described above. Particularly, the inner tube 112 has a stopper 112a. The elastic member 122 of the buffer assembly 120 leans against the stopper 112a. The buffer assembly 120 further includes a universal joint 124 connected between the elastic member 122 and the cutter bit 130. The universal joint 124 allows the cutting portion 132 to be tilted along with the surface of the operated object as described above.

To be more specific, the universal joint 124 provided in the present embodiment is, for instance, a ball joint and includes a first connection member 124a and a second connection member 124b. The cutting bit 130 is connected to the first connection member 124a, and the elastic member 122 is connected to the second connection member 124b. The first connection member 124a has a convex spherical surface S1. The second connection member 124b has a concave spherical surface S2 and is movably connected to the convex spherical surface S1 through the concave spherical surface S2. In the present embodiment, the second connection member 124b has an extension portion E fixed to the stopper 112a, for instance, and the elastic member 122 is sleeved on the extension portion E.

Figure 5:
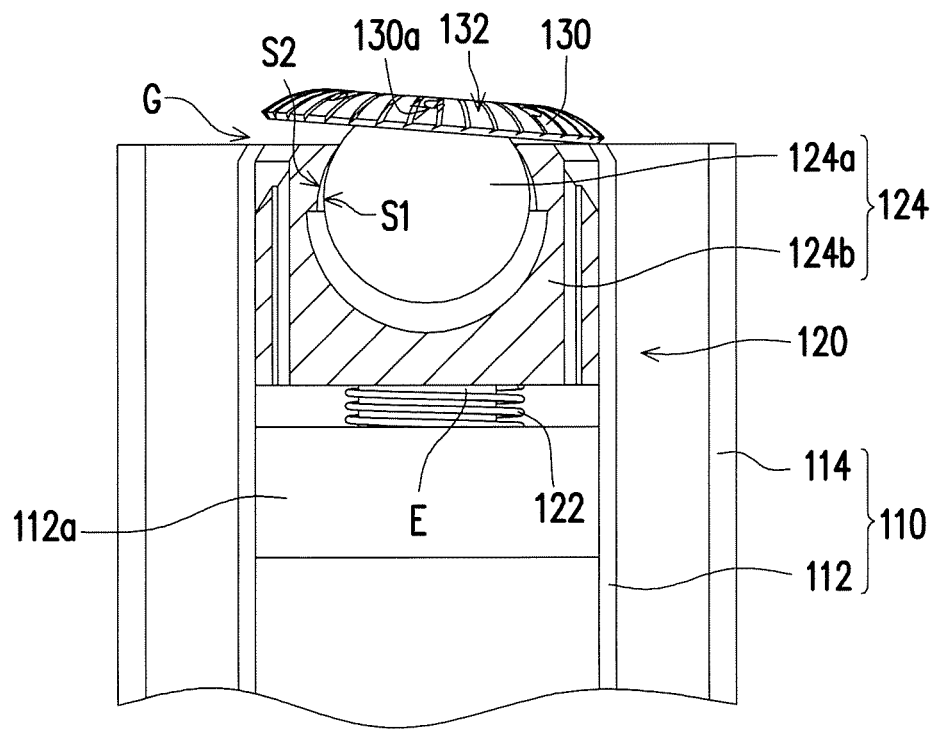
FIG. 5 illustrates a tilted state of the cutter bit depicted in FIG. 4.

FIG. 5 illustrates a tilted state of the cutter bit depicted in FIG. 4. Through the relative sliding between the convex spherical surface S1 and the concave spherical surface S2, the cutter bit 130 may be tilted relatively to the inner tube 112 as shown in FIG. 5. The maximum tilt angle is, for example, 10 degrees to 20 degrees. However, this should not be construed as a limitation to the invention. Besides, the maximum moving distance of the cutter bit 130 derived from the elastic deformation of the elastic member 122 is, for instance, 1 millimeter to 2 millimeters, which should however not be construed as a limitation to the invention as well.

With reference to FIG. 3, the cutter bit 130 provided in the present embodiment has a plurality of holes 130a. After the operated object is cut by the cutting portion 132 of the cutter bit 130, sawdust generated by the cutter bit 130 may be discharged along the main body 110 through the holes 130a. To be specific, the minimally invasive surgical device 100 shown in FIG. 1 includes a suction supply portion 140 which is, for instance, a suction supply interface or a suction supply passage, and is connected to a suction supply, e.g., a pump or other appropriate suction generating devices. Here, the sawdust generated after the operated object is cut by the cutting portion 132 of the cutter bit 130 is adapted to move along the main body 110 by the suction force provided by the suction supply portion 140. A flow passage may be arranged in the main body 110. The flow passage is, for instance, formed inside the inner tube 112 and connected between the suction supply portion 140 and the holes 130a of the cutter bit 130, so as to allow the sawdust to flow. The suction supply portion 140 shown in FIG. 1 is schematic and may be disposed inside the rear end of the outer tube 114 as shown in FIG. 1 or externally connected to the outer tube 114, which should not be construed as a limitation to the invention. In the present embodiment, even though a gap G (shown in FIG. 4) exists between the cutter bit 130 and the main body 110, the suction force provided by the suction supply portion 140 may prevent the sawdust from falling out from the gap G between the cutter bit 130 and the main body 110 after the sawdust passes through the holes 130a.

Figure 6:
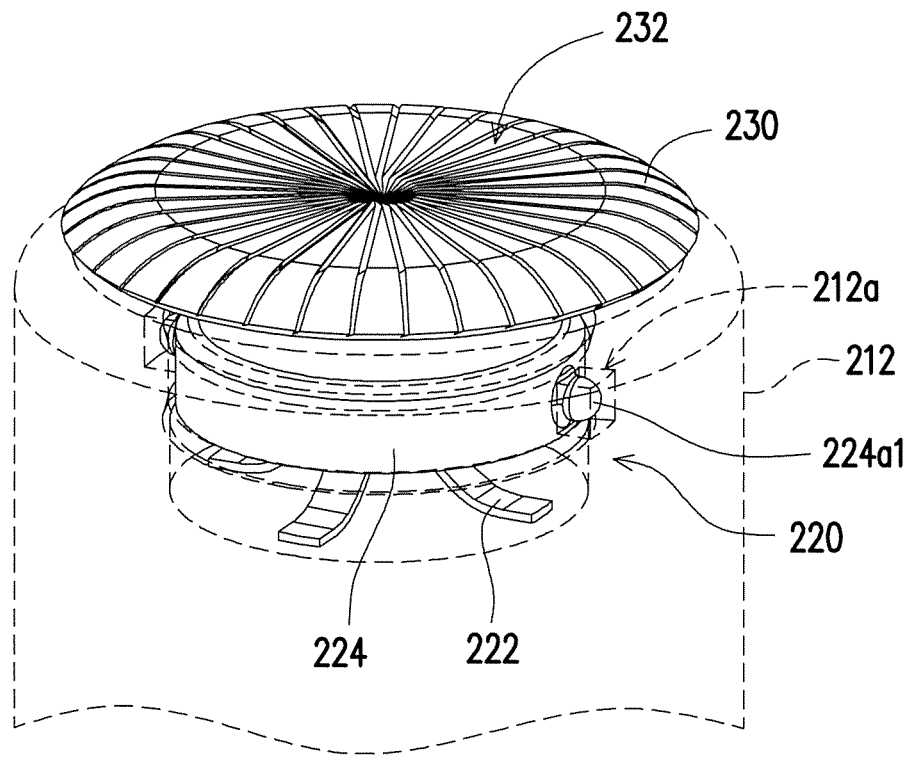
FIG. 6 is a three-dimensional view of some components of a minimally invasive surgical device according to another embodiment of the invention.
Figure 7:
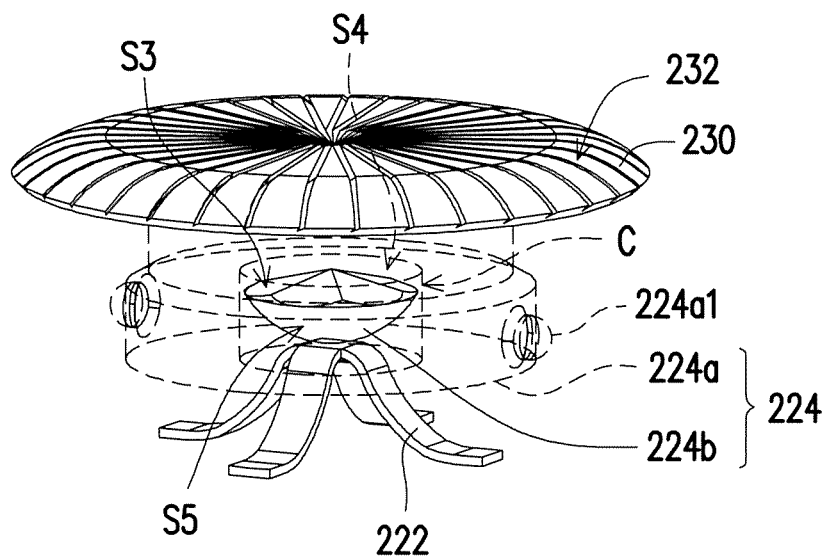
FIG. 7 is a three-dimensional view of the cutter bit and the buffer assembly depicted in FIG. 6.
Figure 8:
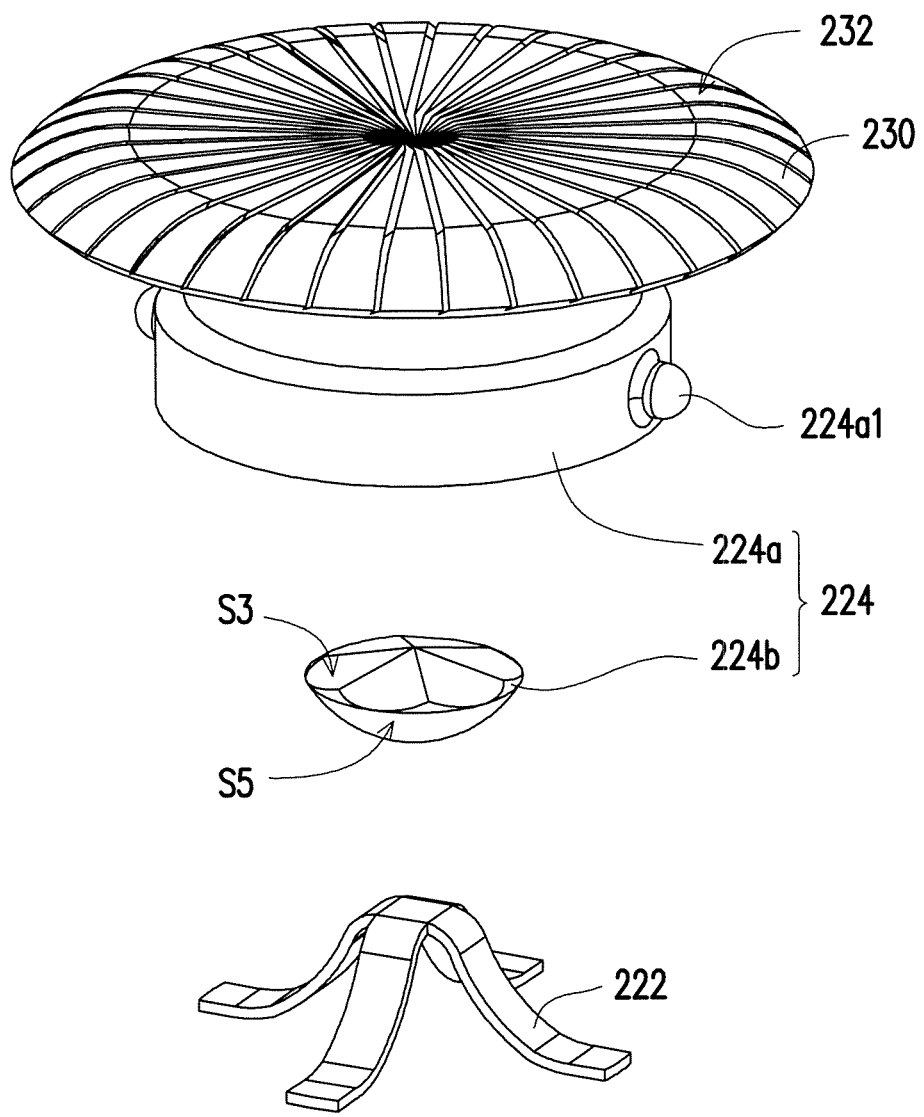
FIG. 8 is an exploded view of the cutter bit and the buffer assembly depicted in FIG. 7.

FIG. 6 is a three-dimensional view of some components of a minimally invasive surgical device according to another embodiment of the invention. FIG. 7 is a three-dimensional view of the cutter bit and the buffer assembly depicted in FIG. 6. FIG. 8 is an exploded view of the cutter bit and the buffer assembly depicted in FIG. 7. According to the embodiments shown in FIG. 6 to FIG. 8, the inner tube 212, the outer tube (not shown in FIG. 6 to FIG. 8 for clarity purposes), the buffer assembly 220, the elastic member 222, the universal joint 224, the cutter bit 230, and the cutting portion 232 are arranged and operated in a manner similar to those of the inner tube 112, the outer tube 114, the buffer assembly 120, the elastic member 122, the universal joint 124, the cutter bit 130, and the cutting portion 132 shown in FIG. 1 to FIG. 5 and thus will not be further described hereinafter.

The difference between the embodiments shown in FIG. 6 to FIG. 8 and the embodiments shown in FIG. 1 to FIG. 5 lies in that the universal joint 224 includes a first connection member 224a and a second connection member 224b. The cutter bit 230 is connected to the first connection member 224a. The elastic member 222 is connected to the second connection member 224b. The first connection member 224a has an accommodation cavity C, and the second connection member 224b has a plurality of inclined surfaces S3 and is movably accommodated in the accommodation cavity C. An inner surface S4 of the accommodation cavity C is adapted to lean against any of the inclined surfaces S3 to enable the first connection member 224a and the cutter bit 230 to be tilted.

Further, the inner tube 212 provided in the present embodiment has two concave portions 212a. The first connection member 224a has two convex portions 224a1 and is movably connected to the concave portions 212a through the convex portions 224a1. The second connection member 224b has an arc surface S5 relative to the inclined surfaces S3 and movably leans against a top end of the elastic member 222 through the arc surface S5, so that the first connection member 224a and the second connection member 224b have enough freedom of operation to drive the cutter bit 230 to be tilted. In addition, the elastic member 222 provided in the present embodiment is a leaf spring and is not the elastic member 122 which is a compression spring as described in the embodiments shown in FIG. 1 to FIG. 5. In other embodiments, the elastic member may be another proper member which may generate elastic deformation, e.g., an elastic polymer member. The invention is not limited thereto.

Figure 9:
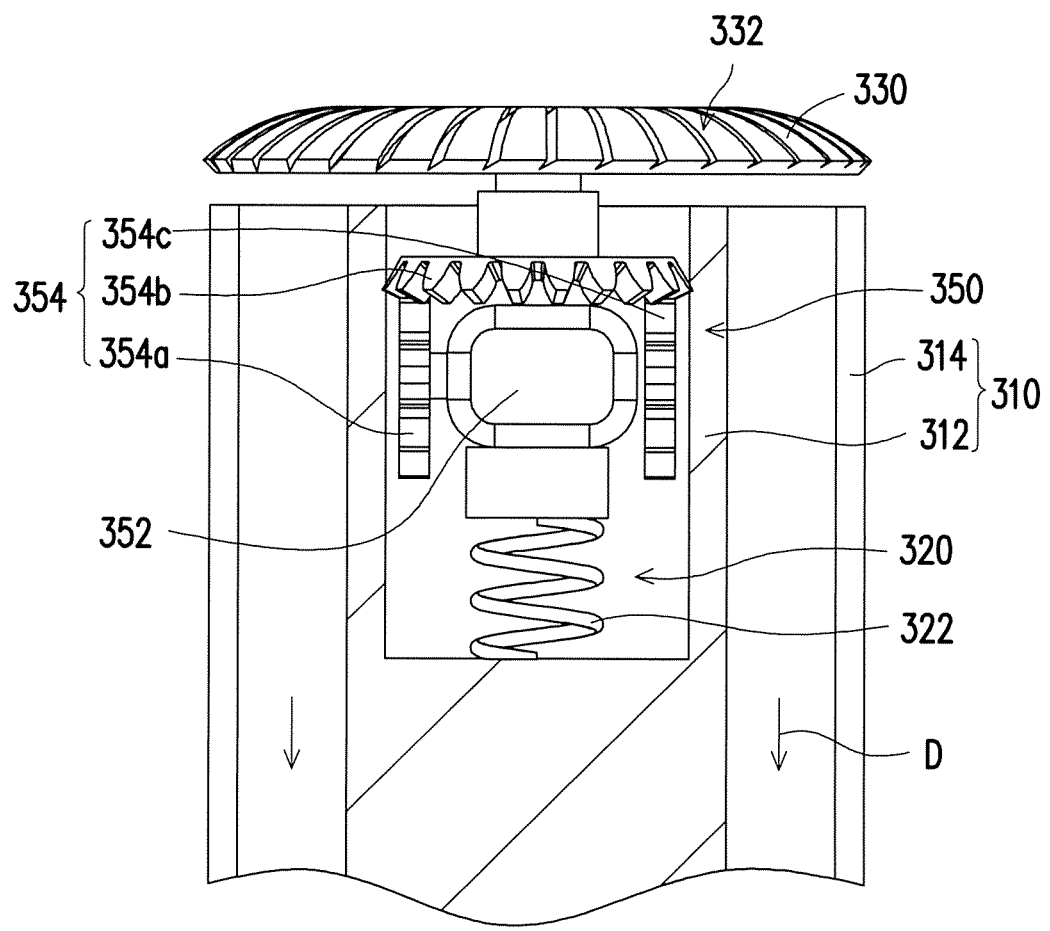
FIG. 9 is a three-dimensional view of some components of a minimally invasive surgical device according to another embodiment of the invention.

FIG. 9 is a three-dimensional view of some components of a minimally invasive surgical device according to another embodiment of the invention. According to the embodiment shown in FIG. 9, the inner tube 312, the outer tube 314, the buffer assembly 320, the elastic member 322, the cutter bit 330, and the cutting portion 332 are arranged and operated in a manner similar to those of the inner tube 112, the outer tube 114, the buffer assembly 120, the elastic member 122, the cutter bit 130, and the cutting portion 132 shown in FIG. 1 to FIG. 5 and thus will not be further described hereinafter.

The difference between the embodiment shown in FIG. 9 and the embodiments shown in FIG. 1 to FIG. 5 is that the buffering assembly 320 does not have the universal joint 124 shown in FIG. 1 to FIG. 5, and the cutter bit 330 is tilted by virtue of the elastic deformation of the elastic member 322. Besides, the inner tube 312 provided in the present embodiment is equipped with a driver unit 350, while the driver unit is externally connected to the inner tube 112 provided in the embodiments shown in FIG. 1 to FIG. 5. Specifically, the driver unit 350 is connected between the elastic member 322 of the buffer assembly 320 and the cutter bit 330, and is adapted to drive the cutter bit 330 to rotate relatively to the inner tube 312. The driver unit 350 includes an actuator 352 and a gear set 354. The actuator 352 is, for example, a motor and is connected to the elastic member 322 of the buffer assembly 320. The gear set 354 includes a driving gear 354a and a driven gear 354b and connected between the actuator 352 and the cutter bit 330, so that the actuator 352 may sequentially drive the cutter bit 330 to rotate sequentially through the driving gear 354a and the driven gear 354b. Besides, the gear set 354 may further include a driven gear 354c symmetrical to the driving gear 354a, so that the operation of the gear set 354 is relatively balanced and stable.

Moreover, where the cutter bit 330 provided in the present embodiment has the holes 130a as shown in FIG. 3, a corresponding flow path may be formed between the inner tube 312 and the outer tube 314, so that the sawdust may flow along the direction D shown in FIG. 9; however, this should not be construed as a limitation to the invention.

Figure 10:
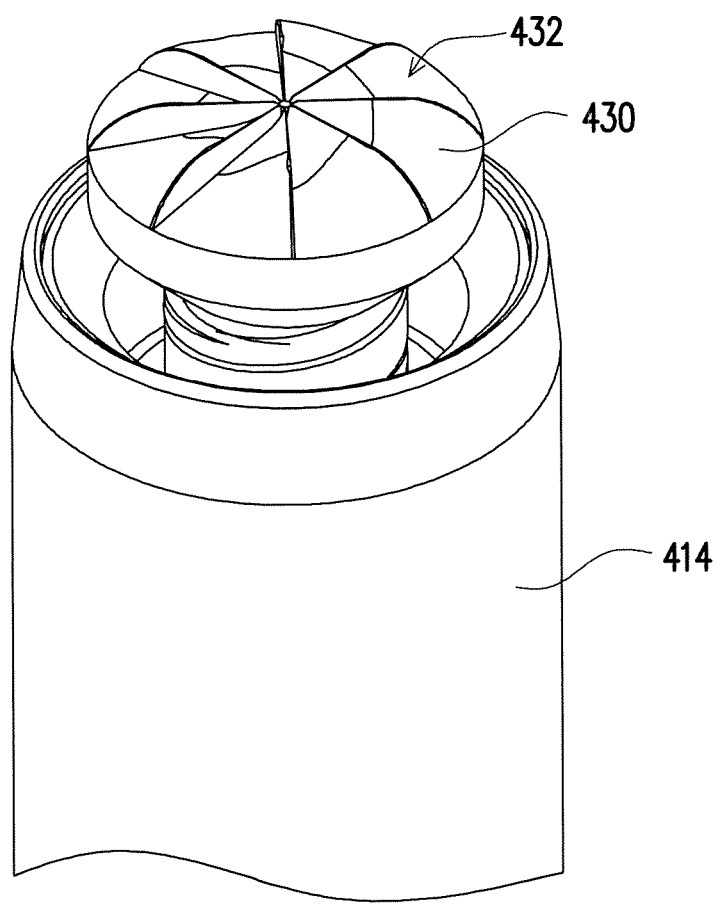
FIG. 10 is a three-dimensional view of a portion of a minimally invasive surgical device according to another embodiment of the invention.
Figure 11:
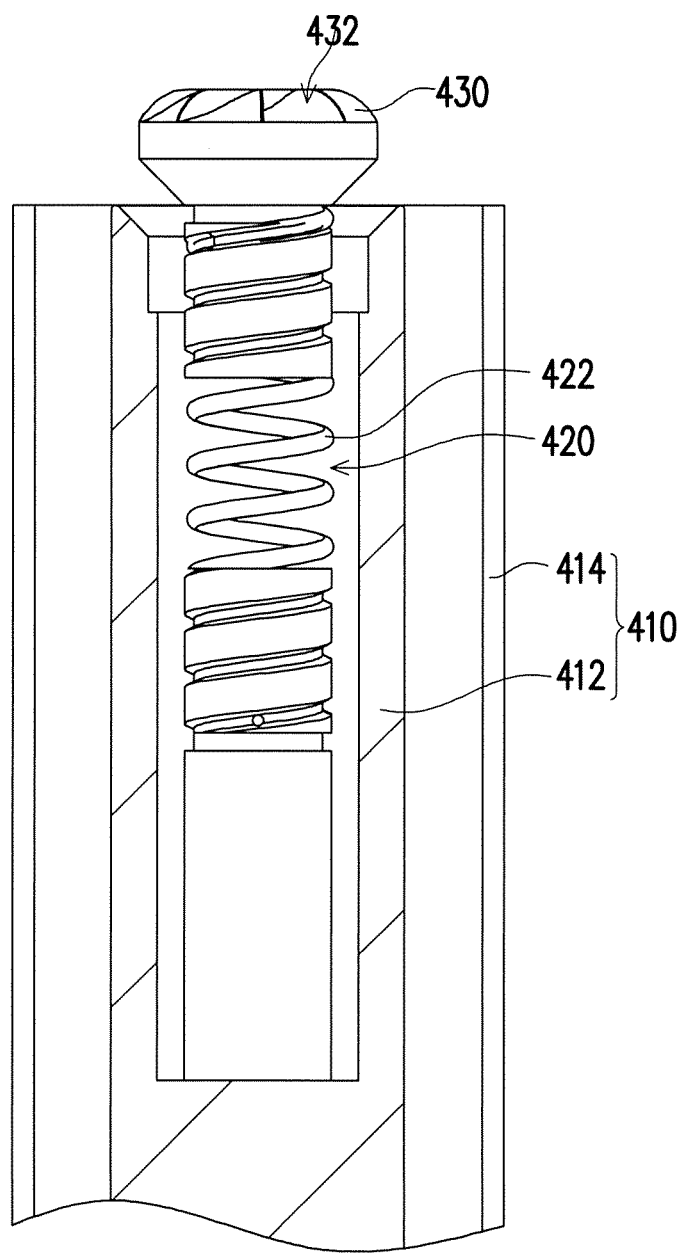
FIG. 11 illustrates a partial structure of the minimally invasive surgical device depicted in FIG. 10.

FIG. 10 is a three-dimensional view of a portion of a minimally invasive surgical device according to another embodiment of the invention. FIG. 11 illustrates a partial structure of the minimally invasive surgical device depicted in FIG. 10. According to the embodiments shown in FIG. 10 and FIG. 11, the inner tube 412, the outer tube 414, the buffer assembly 420, the elastic member 422, the cutter bit 430, and the cutting portion 432 are arranged and operated in a manner similar to those of the inner tube 112, the outer tube 114, the buffer assembly 120, the elastic member 122, the cutter bit 130, and the cutting portion 132 shown in FIG. 1 to FIG. 5 and thus will not be further described hereinafter.

The difference between the embodiments shown in FIG. 10 and FIG. 11 and the embodiments shown in FIG. 1 to FIG. 5 is that the buffering assembly 420 does not have the universal joint 124 shown in FIG. 1 to FIG. 5, and the cutter bit 430 is tilted by virtue of the elastic deformation of the elastic member 422. In addition, the cutting portion 432 of the cutter bit 430 provided in the present embodiment is constituted by a plurality of blade structures; by contrast, the cutting portion 132 of the cutter bit 130 shown in FIG. 3 is constituted by a plurality of indented structures. In other embodiments, the cutting portion of the cutter head may be in another suitable form, which is not limited in the invention.

It will be apparent to those skilled in the art that various modifications and variations can be made to the structure described in the invention without departing from the scope or spirit of the invention. In view of the foregoing, it is intended that the invention cover modifications and variations provided they fall within the scope of the following claims and their equivalents.

What is claimed is:

1. A minimally invasive surgical device comprising:
   a main body comprising an inner tube and an outer tube, the inner tube being disposed in the outer tube;
   an elastic assembly, one end of the elastic assembly being connected to the inner tube; and
   a cutter bit connected to an opposite end of the elastic assembly and having a cutting portion, wherein when the cutting portion is in contact with an object, the elastic assembly is adapted to enable the cutter bit to move relatively to the inner tube to decrease a cutting force between the cutting portion and the object, and is adapted to enable the cutting portion to be tilted along with a surface of the object,
   wherein the elastic assembly comprises an elastic member and a universal joint, the elastic assembly connects the inner tube and the cutter bit and is at least partially disposed in the inner tube, the universal joint is connected between the elastic member and the cutter bit, the elastic member of the elastic assembly is entirely located inside the inner tube, and the elastic member is located outside the universal joint, and
   the universal joint is slidably disposed in the inner tube along a direction parallel to a center axis of the inner tube, the center axis passes through the universal joint, the cutting portion is located on an upper surface of the universal joint and is extended outward from the center axis along a radial direction of the center axis.

2. The minimally invasive surgical device according to claim 1, wherein the elastic member is a compression spring, a leaf spring, or elastic polymer.

3. The minimally invasive surgical device according to claim 1, wherein the universal joint comprises a first connection member and a second connection member, the first connection member has a convex spherical surface, the second connection member has a concave spherical surface and is movably connected to the convex spherical surface through the concave spherical surface, the cutter bit is connected to the first connection member, and the elastic member is connected to the second connection member.

4. The minimally invasive surgical device according to claim 1, wherein the universal joint comprises a first connection member and a second connection member, the first connection member has an accommodation cavity, the second connection member has a plurality of inclined surfaces and is movably disposed in the accommodation cavity, an inner surface of the accommodation cavity is adapted to lean against any of the plurality of inclined surfaces to enable the first connection member to be tilted, the cutter bit is connected to the first connection member, and the elastic member is connected to the second connection member.

5. The minimally invasive surgical device according to claim 4, wherein the inner tube has at least one concave portion, and the first connection member has at least one convex portion and is movably connected to the at least one concave portion through the at least one convex portion.

6. The minimally invasive surgical device according to claim 4, wherein the second connection member has an arc surface relative to the plurality of inclined surfaces and movably leans against the elastic member through the arc surface.

7. The minimally invasive surgical device according to claim 1, further comprising a driver unit adapted to drive the cutter bit to rotate.

8. The minimally invasive surgical device according to claim 7, wherein the driver unit is connected between the elastic assembly and the cutter bit and adapted to drive the cutter bit to rotate relatively to the inner tube.

9. The minimally invasive surgical device according to claim 8, wherein the driver unit comprises an actuator and a gear set, the actuator is connected to the elastic assembly, and the gear set is connected between the actuator and the cutter bit.

10. The minimally invasive surgical device according to claim 8, wherein the driver unit is connected to the inner tube and adapted to drive the inner tube and the cutter bit to rotate together relatively to the outer tube.

11. The minimally invasive surgical device according to claim 1, wherein the cutter bit has at least one hole, and sawdust generated after the object is cut by the cutting portion is discharged along the main body through the at least one hole.

12. The minimally invasive surgical device according to claim 11, comprising a suction supply portion, wherein the sawdust generated after the object is cut by the cutting portion is adapted to move along the main body by a suction force provided by the suction supply portion.

13. The minimally invasive surgical device according to claim 1, wherein an outer diameter of the cutter bit is less than 10 millimeters.

14. The minimally invasive surgical device according to claim 1, wherein the inner tube has a stopper, and the elastic assembly leans against the stopper.

* * * * *